United States Patent [19]

Bronstein et al.

[11] Patent Number: 5,089,630
[45] Date of Patent: Feb. 18, 1992

[54] DIOXETANES FOR USE IN ASSAYS

[76] Inventors: Irena Y. Bronstein, 11 Ivanhoe St., Newton, Mass. 02158; Brooks Edwards, 28 Inman St. Apt. 5, Cambridge, Mass. 02139; Larry Kricka, 880 Nathan Hale Rd., Berwyn, Pa. 19312; John Voyta, 20 Williams Rd., North Reading, Mass. 01864

[21] Appl. No.: 512,030

[22] Filed: Apr. 13, 1990

Related U.S. Application Data

[63] Continuation of Ser. No. 140,035, Dec. 31, 1987, abandoned.

[51] Int. Cl.$^5$ .................. C07D 493/10; C07F 9/665
[52] U.S. Cl. ........................... 549/220; 549/332; 548/113; 536/18.1
[58] Field of Search .............. 549/220, 332; 548/113; 536/18.1

[56] References Cited

U.S. PATENT DOCUMENTS

4,857,652 8/1989 Schaap .................. 549/510

FOREIGN PATENT DOCUMENTS

0254051 1/1988 European Pat. Off. .

OTHER PUBLICATIONS

Adam et al., Agnew, Chem. Int. Ed. Engl. 26:796 (1987).
Schaap et al., Tetrahedron Lett. 28:1159 (1987).

*Primary Examiner*—Richard L. Raymond
*Attorney, Agent, or Firm*—Oblon, Spivak, McClelland, Maier & Neustadt

[57] ABSTRACT

A dioxetane that includes a fluorescent chromophore spiro-bound at the 4-carbon of the dioxetane. The dioxetane has the formula

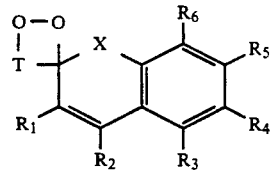

where X is $CR_7R_8$, O, S, or N-R (where each $R_7$, $R_8$, and R, independently, is H, alkyl, heteroalkyl, aryl, heteroaryl, cycloalkyl, cycloheteroalkyl, aralkyl, alkaryl, or an enzyme cleavable group), and each $R_1$, $R_2$, $R_3$, $R_4$, $R_5$, and $R_6$, independently, is H, an electron-withdrawing group, an electron-donating group, heteroaryl, or an enzyme cleavable group, or groups $R_1$–$R_6$ together form a ring, and T is a substituted or unsubstituted aryl, polyaryl, cycloalkylidene or polycycloalkylidene group spiro-bound at the 3-carbon of the dioxetane.

The dioxetane can be decomposed by direct cleavage of the dioxetane O—O bond or by cleavage of an enzyme cleavable group bonded to the dioxetane to form a luminescent substance that includes the coumarin portion of the dioxetane.

The dioxetanes are used in an assay to detect a member of a specific binding pair or an enzyme.

31 Claims, No Drawings

DIOXETANES FOR USE IN ASSAYS

This application is a continuation of application Ser. No. 140,035 filed Dec. 31, 1987, now abandoned.

BACKGROUND OF THE INVENTION

This invention relates to using dioxetanes to detect a substance in a sample.

Dioxetanes are compounds having a 4-membered ring in which 2 of the members are oxygen atoms bonded to each other. Dioxetanes can be thermally or photochemically decomposed to form carbonyl products, e.g., ketones or aldehydes. Release of energy in the form of light (i.e. luminescence) accompanies the decompositions.

SUMMARY OF THE INVENTION

In general, the invention features a dioxetane having the formula

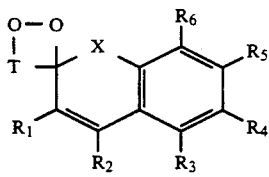

(1)

where T is a substituted (e.g., containing one or more $C_1$-$C_7$ alkyl groups, heteroatom containing groups, e.g., carbonyl groups or enzyme cleavable groups, i.e. groups having a bond that can be cleaved by an enzyme to yield an electron-rich moiety bonded to the dioxetane, e.g., phosphate) or unsubstituted aryl (having between 6 and 12 carbon atoms, inclusive, in the ring, e.g., phenyl), polyaryl (having 2 or more rings, e.g., naphthyl), cycloalkylidene (having between 6 and 12 carbon atoms, inclusive, in the ring) or a polycycloalkylidene (having 2 or more fused rings, each ring independently having between 5 and 12 carbon atoms, inclusive) spiro-bound group at the 3-carbon of the dioxetane; X is $CR_7R_8$, O, S, or N—R (where each $R_7$, $R_8$, and R, independently, is H; a branched or straight chain alkyl group having between 1 and 20 carbon atoms, inclusive, e.g., methyl; a branched or straight chain heteroalkyl having between 1 and 7 carbon atoms, inclusive, e.g., methoxy, hydroxyethyl, or hydroxypropyl; aryl having 1 or 2 rings, e.g., phenyl; heteroaryl having 1 or 2 rings, e.g., pyrrolyl or pyrazolyl; cycloalkyl having between 3 and 7 carbon atoms, inclusive, in the ring, e.g., dioxane; aralkyl having 1 or 2 rings, e.g., benzyl; alkaryl having 1 or 2 rings, e.g., tolyl; or an enzyme cleavable group as defined above); and each $R_1$, $R_2$, $R_3$, $R_4$, $R_5$, and $R_6$, independently, can be H; an electronwithdrawing group (e.g., perfluoroalkyl having between 1 and 7 carbon atoms, inclusive, e.g., trifluoromethyl; halogen; $CO_2H$, $ZCO_2H$, $SO_3H$, $ZSO_3H$, $NO_2$, $ZNO_2$, C≡N, or ZC≡N, where Z is a branched or straight chain alkyl group having between 1 and 7 carbon atoms, inclusive, e.g., methyl, or an aryl group having 1 or 2 rings, e.g., phenyl); an electron-donating group (e.g., a branched or straight chain $C_1$-$C_7$ alkoxy, e.g., methoxy or ethoxy; aralkoxy having 1 or 2 rings, e.g., phenoxy; a branched or straight chain $C_1$-$C_7$ hydroxyalkyl, e.g., hydroxymethyl or hydroxyethyl; hydroxyaryl having 1 or 2 rings, e.g., hydroxyphenyl; a branched or straight chain $C_1$-$C_7$ alkyl ester, e.g, acetate; or aryl ester having 1 or 2 rings, e.g., benzoate); heteroaryl having 1 or 2 rings, e.g., benzoxazole, benzthiazole, benzimidazole, or benztriazole; or an enzyme cleavable group as defined above. Furthermore, groups $R_1$-$R_6$ together can form a ring, which can be substituted or unsubstituted. Where group T is an aryl or polyaryl group, obviously that aryl group must be one whose structure permits spiro linkage, and thus groups, e.g., phenyl, which cannot be spiro-linked, are excluded.

In addition, as will become apparent from the text which follows, where triggering of the dioxetane is to be by cleavage of the 0-0 bond of the dioxetane ring, neither group T nor the luminescent moiety containing group $R_1$-$R_6$ need contain an enzyme-cleavable group. Where triggering is by cleavage of an enzyme-cleavable group, either T or the luminescent moiety must contain such a group.

The dioxetane is capable of decomposing to form a luminescent substance (i.e. a substance that emits energy in the form of light) having the formula

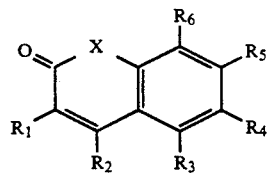

(2)

The invention also features various compounds useful as intermediates in synthesizing the dioxetanes.

In preferred embodiments, group X is O, groups $R_1$-$R_3$ and $R_6$ are H, and groups $R_4$ and $R_5$, independently, are phosphate or H. Group T of the dioxetane is preferably an adamantylidene group. The dioxetane also preferably includes an enzyme cleavable group which may be bonded to group T or to the fluorescent chromophore portion of the dioxetane (preferably at $R_5$).

The dioxetanes are used in an assay method in which a member of a specific binding pair (i.e. two substance that bind specifically to each other) is detected by means of an optically detectable reaction. According to this method, the dioxetane is contacted with an enzyme that causes the dioxetane to decompose to form a luminescent substance (i.e. a substance that emits energy in the form of light). The luminescent substance, which has the formula

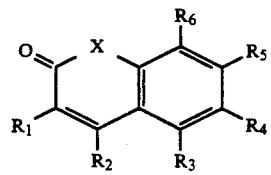

(3)

is detected as an indication of the presence of the first substance. By measuring the intensity of luminescence, the concentration of the first substance can be determined.

Where the enzyme is an oxido-reductase (preferably a peroxidase, e.g., horseradish peroxidase or microperoxidase), it causes the dioxetane to decompose by cleaving the 0—0 bond of the 4-membered ring portion of the dioxetane. The enzyme can act directly on the dioxetane substrate or can be mediated through the addition of peroxide. This method can be used to decompose not just dioxetanes of formula (1), but to decompose any dioxetanes having the general formula

 (4)

where V is a fluorescent chromophore which is either spiro-bound at the 4-carbon of the dioxetane or is bonded to the 4-carbon of the dioxetane through a non-spiro linkage.

Where the dioxetane includes an enzyme cleavable group (e.g., phosphate), the enzyme (e.g., phosphatase) causes the dioxetane to decompose by cleaving the enzyme cleavable group from the dioxetane. Cleavage yields a negatively charged atom (e.g., an oxygen atom) bonded to the dioxetane, which in turn destabilizes the dioxetane, causing it to decompose and emit radiation, which in turn is absorbed by the portion of the molecule containing the fluorescent chromophore, which consequently luminesces.

Preferred specific binding pairs for which the above-described assay method is useful include an antigen-antibody pair, and a pair consisting of a nucleic acid and a probe capable of binding to all or a portion of the nucleic acid. The dioxetanes are also useful in an assay method for detecting an enzyme in a sample.

The invention provides a simple, very sensitive method for detecting substances in samples, e.g., biological samples, and is particularly useful for substances present in low concentrations. Because dioxetane decomposition serves as the excitation energy source for the coumarin chromophore, an external excitation energy source, e.g., light, is not necessary.

Enzyme-triggered decomposition allows for high sensitivity because one enzyme molecule can cause many dioxetane molecules to luminesce, thus creating an amplification effect. In addition, through appropriate modifications of the T group and fluorescent chromophore, the solubility of the dioxetane and the kinetics of dioxetane decomposition can be varied. The dioxetanes can also be attached to a variety of molecules, e.g., proteins or haptens, or immobilization substrates, e.g., polymer membranes, or included as a side group in a homopolymer or copolymer.

The spiro linkage joining the chromophore to the 4-membered ring portion of the dioxetane stabilizes the dioxetane prior to enzyme activation, making it easy to store the dioxetane for extended periods of time. By using coumarin as the fluorescent chromophore, good quantum yields of luminescence are obtained (as used herein, "quantum yield" refers to the number of photons emitted from the luminescent product per number of moles of dioxetane decomposed). The coumarin-substituted dioxetane molecules are also readily synthesized in good yield.

A further advantage is that where the enzyme acts directly on the O—O bond, engineering of the emitting chromophore (group V) is not necessary.

Other features and advantages of the invention will be apparent from the following description of the preferred embodiments thereof, and from the claims.

DESCRIPTION OF THE PREFERRED EMBODIMENTS

We now describe the structure, synthesis, and use of preferred embodiments of the invention.

Structure

The invention employs dioxetanes having the formula

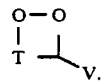

The purpose of group T is to stabilize the dioxetane, i.e. to prevent premature decomposition. Large, bulky, sterically hindered molecules, e.g., fused polycyclic molecules, are the most effective stabilizers. In addition, T preferably contains only C—C and C—H single bonds. The most preferred molecule is an adamantylidene group consisting of 3 fused cyclohexyl rings. The adamantylidene group is spiro-bound at the 3-carbon of the dioxetane.

Group V is a fluorescent chromophore which is either spiro-bound at the 4-carbon of the dioxetane or bonded to the 4-carbon of the dioxetane through a non-spiro linkage. It becomes luminescent when enzymatic cleavage, either of an enzyme cleavable group bonded to group T or group V, or of the O—O bond of the 4-membered dioxetane ring, occurs to cause decomposition of the dioxetane. The decomposition produces two individual carbonyl-containing compounds, one of which contains group T, and the other of which contains group V; the energy released form dioxetane decomposition causes the chromophore to luminesce. Preferably, the excited state energy of group V (i.e. the energy it must possess in order to emit light) is less than the excited state energy of the ketone containing group T in order to confine luminescence to group V.

The preferred dioxetane has the formula

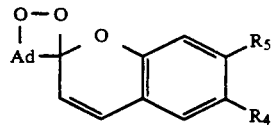

where $R_4$ and $R_5$ independently, are H or phosphate and Ad is an adamantylidene group. Decomposition yields a coumarin molecule having the formula

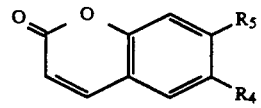

whose excited state energy is less than that of spiroadamantanone (the other decomposition product).

The dioxetanes are generally decomposed in two ways. One way is to add an oxido-reductase enzyme, e.g., a peroxidase (preferably horseradish or microperoxidase); the enzyme cleaves the O—O bond of the 4-membered ring, thereby generating the luminescent molecule.

A second way is to bond an enzyme cleavable group to group T or, more preferably, to group V. Contact with the appropriate enzyme cleaves the enzyme-cleavable bond, yielding an electron-rich moiety bonded to group V or group T; this moiety initiates the decomposition of the dioxetane into 2 individual carbonyl-containing compounds. Examples of electron-rich moieties include oxygen, sulfur, and amine or amido anions. The most preferred moiety is an oxygen anion. Examples of suitable enzyme-cleavable groups, and the enzymes specific to these groups, are given below in Table 1; an arrow denotes the enzyme-cleavable bond. The most preferred group is a phosphate ester, which is cleaved by alkaline or acid phosphatase enzymes.

TABLE 1

| Group Z | Enzyme |
|---|---|
| 1) 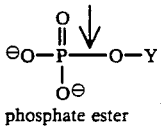 phosphate ester | alkaline and acid phosphatases |
| 2) 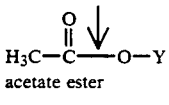 acetate ester | esterases |
| 3) 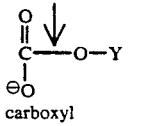 carboxyl | decarboxylases |
| 4) 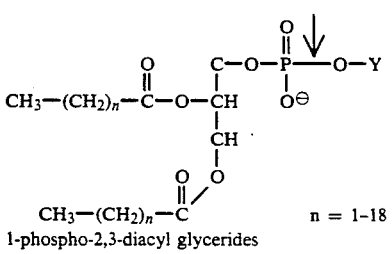 1-phospho-2,3-diacyl glycerides    n = 1–18 | phospholipase D |
| 5) 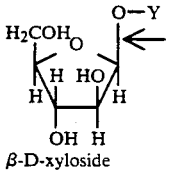 β-D-xyloside | β-xylosidase |
| 6) 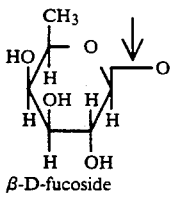 β-D-fucoside | β-D-fucosidase |
| 7) 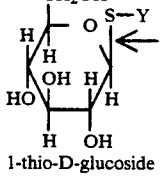 1-thio-D-glucoside | thioglucosidase |
| 8) 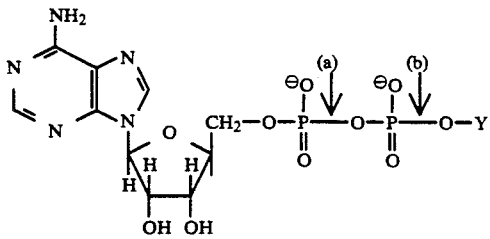 adenosine diphosphate analogs. | ADPase (a) + phosphatase (b) |

TABLE 1-continued
| Group Z | Enzyme |
|---|---|
| 9) 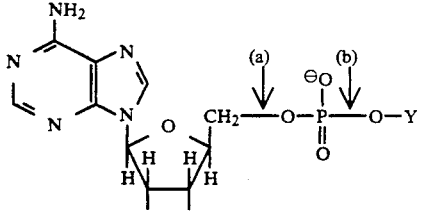 adenosine monophosphate analogs | AMPase (a) + phosphatase (b) |
| 10) 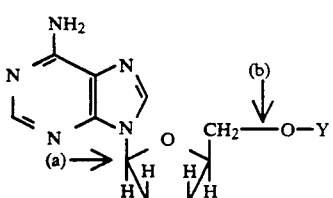 adenosine analogs | 5'-nucleosidase (a) + ribosidase (b) |
| 11) 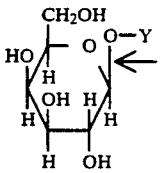 β-D-galactoside | β-D-galactosidase |
| 12) 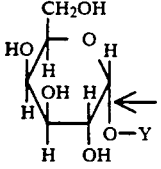 α-D-galactoside | α-D-galactosidase |
| 13) 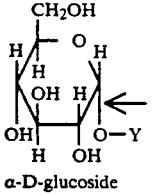 α-D-glucoside | α-D-glucosidase |
| 14) 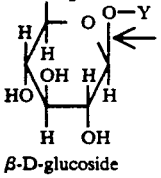 β-D-glucoside | β-D-glucosidase |
| 15) 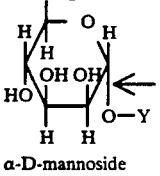 α-D-mannoside | α-D-mannosidase |

TABLE 1-continued

| Group Z | Enzyme |
|---|---|
| 16) 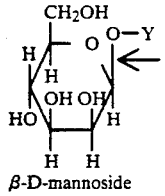 β-D-mannoside | β-D-mannosidase |
| 17) 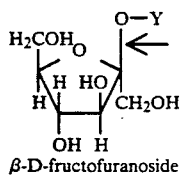 β-D-fructofuranoside | β-D-fructofuranosidase |
| 18) 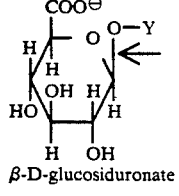 β-D-glucosiduronate | β-D-glucosiduronase |
| 19) 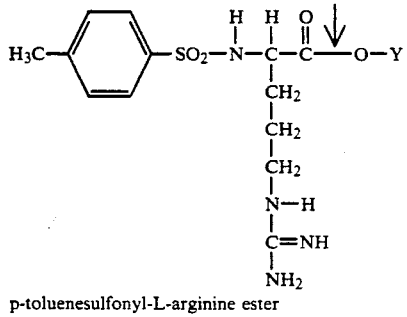 p-toluenesulfonyl-L-arginine ester | trypsin |
| 20) 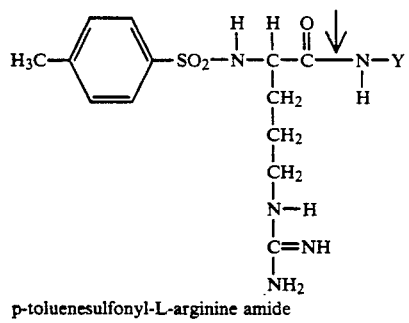 p-toluenesulfonyl-L-arginine amide | trypsin |
| 21) 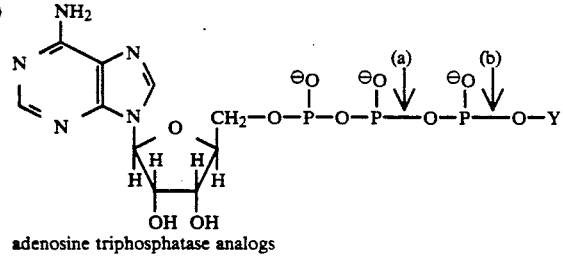 adenosine triphosphatase analogs | ATPase (a) + phosphatase (b) |

Preferably, the enzyme is covalently bonded to a substance having a specific affinity for the substance being detected. Examples of specific affinity substances include antibodies, e.g., anti-hCG, where the substance being detected is an antigen, e.g., hCG; antigens, e.g., hCG, where the substance being detected is an antibody, e.g., anti-hCG; or a probe capable of binding to all or a portion of a nucleic acid, e.g., DNA or RNA, being detected. Bonding is preferably through an amide bond.

Synthesis

In general, the dioxetanes of the invention are synthesized in two steps. The first step involves synthesizing an appropriately substituted olefin having the formula

where T and V are as described above. Olefins in which V is bonded via a non-spiro linkage to the olefin double bond are synthesized according to the method described in Edwards, U.S. Ser. No. 140,197, filed the same day as the present application and assigned to the same assignee, now abandoned, hereby incorporated by reference.

Olefins in which chromophore V is spiro-bound at the olefin double bond are generally synthesized using one of the following two synthetic methods.

The first synthesis involves using the following reaction sequence:

then removed under reduced pressure. The crude acid chloride was diluted with 25 mL sieve dried (3A) pyridine to provide a slightly cloudy, yellow solution upon cooling in an ice bath.

2'-hydroxy-4'-methoxyacetophenone (1.18 g., 7.12 mmole) in 5 mL pyridine was added to the solution dropwise. The mixture was stirred at 0° C. for 30 minutes and then warmed to room temperature for an additional 2 hours. The mixture was poured into saturated $NaHCO_3$ solution (150 mL) and extracted with (3×20 mL) 25% ethyl acetate in hexanes. The combined organics were washed with 1 N HCl, saturated $NaHCO_3$, and water, followed by drying over $Na_2SO_4$. The solution was concentrated to provide 2.5 g. of a yellow oil. I.R. (film):2900 cm$^{-1}$ (ester C=O), 1672 cm$^{-1}$ (ketone C=O). TLC analysis showed that the ester product, 2'-(Adamantane-2-carbonyloxy)-4'-methoxyacetophenone, was sufficiently pure for subsequent use.

The ester obtained above (1.53 g., 4.6 mmol) was next dissolved in 10 mL DMSO, and added dropwise to a suspension of NaH (60% dispersion - .56 g, 13.97 mmole) in 35 mL DMSO. After foaming had ceased, the brown mixture was stirred for 30 minutes at room

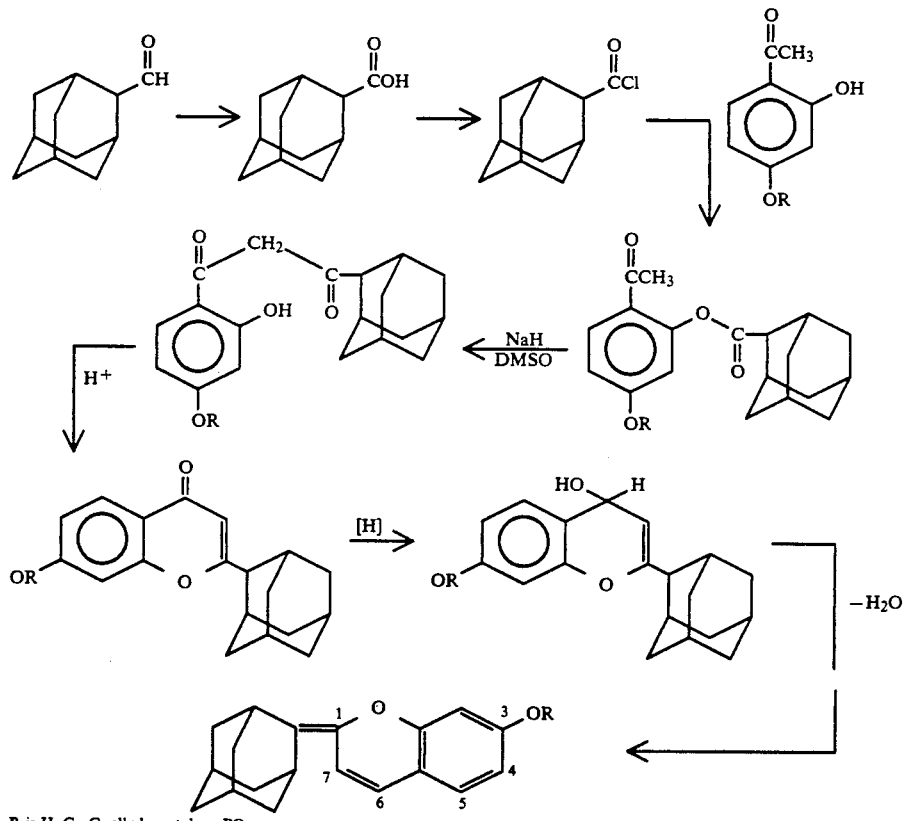

R is H, $C_1$–$C_5$ alkyl, acetyl, or $PO_4$

The reaction was carried out as follows for the case where R is methyl.

Adamantane-2-carboxylic acid (1.51 g., 8.38 mmol), prepared following the procedure of Farcasiu (Synthesis, 1972, 615), was dissolved in 35 mL $CH_2CL_2$. The solution was cooled in an ice bath to produce a thin suspension. Oxalyl chloride (.88 mL, 10 mmol) was added with stirring. The subsequent addition of 2 drops DMF produced immediate evolution of gas. After 15 minutes the mixture was warmed to room temperature and stirring as continued for 2 hours. The volatiles were temperature. The mixture was poured into saturated oxalic acid solution, and extracted with 3×50 mL ethyl acetate. The combined organics were washed several times with water and finally with saturated NaCl. Concentration and chromatography through a short silica gel plug using 10% ethyl acetate in hexanes provided 1.58 g. of a slightly orange solid. I.R. (CHCl$_3$):2900 cm$^{-1}$, 1695 cm$^{-1}$ (C=O). An analytical sample of the product 1,3-diketone, 2-(Adamantane-2-carbonyl)-2'- hydroxy-4'-methoxyacetophenone, recrystallized from hexanes exhibited a melting point of 105°-108° C.

The second synthesis involves using the Barton reaction according to the following reaction sequence:

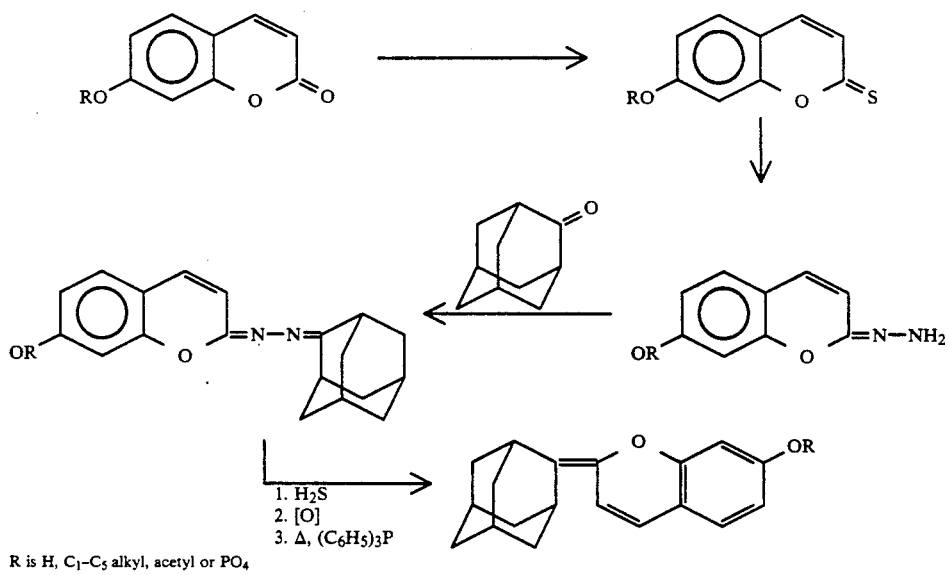

R is H, $C_1-C_5$ alkyl, acetyl or $PO_4$

The crude diketone product of the previous reaction (1.58 g) was suspended in 40 mL acetic acid and treated with 15 drops conc. HCl. The mixture was heated at 100°-110° C. for 30 minutes. The mixture was carefully neutralized with $NaHCO_3$ solution and extracted several times with ethyl acetate. The combined organic layers were washed with water and saturated NaCl. The solution was dried quickly over $Na_2SO_4$ and evaporated to yield 1.5 g of a slightly brown solid which could be recrystallized from ethyl acetate to give .92 gms. of the chromenone, 2-(Adamant-2-yl)-7-methoxy-4H-chromen4-one, as light buff crystals. I.R. ($CHCl_3$) 2900 $cm^{-1}$, 1630 $cm^{-1}$ (C=O), 1595 $cm^{-1}$, 1435 $cm^{-1}$, m.p. 160°-162° C.

A solution of the above-prepared chromenone (0.62 g., 2 mmol) in 10 mL absolute methanol, was treated with 0.4 m $CeCl_3.7H_2O$ in methanol (5 mL, 2 mmol). $NaBH_4$ (76 mg., 2 mmol) was added in small portions with stirring. After 60 minutes at room temperature, 50 mL water was added and the mixture extracted with 2×20 mL ethyl acetate. The combined organic layers were washed first with water and then with saturated NaCl. The solution was dried over $Na_2SO_4$ and concentrated in vacuo to provide the crude allylic alcohol. The light straw colored oil showed no carbonyl absorption (1630 $cm^{-1}$) due to the starting material in the I.R. spectrum. The oil was dissolved in 25 mL $CH_2Cl_2$ under argon and the solution was cooled to −20° C. Triethylamine (0.61 g, 6 mmole) was added by syringe with stirring. Methanesulfonyl chloride (0.25 g., 2.2 mmole) was then added dropwise. The mixture was allowed to slowly warm up to room temperature, whereupon stirring was continued overnight. The mixture was extracted several times with water, dried over $Na_2SO_4$, and stripped to remove solvent and excess triethylamine. The product, 7-methoxy-2-adamantylidene-3-chromene, was obtained with a yield of 0.5 g. To prepare the phosphorylated version, the chromene is demethylated with sodium ethanethiolate in DMF, and then phosphorylated with 2-chloro-2-oxo-1,3-dioxaphospholane as described in Edwards, U.S. Ser. No. 140,197, described earlier, now abandoned.

The reaction was carried out as follows for the case where R is methyl.

7-methoxy-coumarin-2-thione (2 g, 10.4 mmol), obtained by the procedure of F. Tiemann (Ber. 19, 1661, 1886), and hydrazine monohydrate (.55 mL, 11.3 mmol) were heated under reflux in absolute ethanol for 4 hours. The mixture was filtered while hot and the filtrate evaporated under reduce pressure. The residue was extracted several times with boiling petroleum ether (35°-60° C.). The solution was concentrated to dryness and the residue was recrystallized from ethanol to provide the hydrazone, 2-hydrazono-7-methoxy-2H-benzopyran, as a light yellow solid.

A solution of the above hydrazone (2. g., 10.5 mmol) and 2-adamantanone (1.6 g, 10.7 mmol) in 50 mL absolute ethanol was treated with 0.1 mL triethylamine and 0.1 mL glacial acetic acid. The mixture was stirred overnight at room temperature and subsequently refluxed for 3 hours. The solvent was removed and the residue was chromatographed on silica gel to obtain the mixed azine, 7-methoxy-2-N-benzo-2H-pyranoadamantylideneazine, as a yellow solid.

The azine (3.2 g, 10 mmol) was dissolved in 200 mL of 1:1 toluene-dimethoxyethane. This solution was then treated with 2 mg. of p-toluene sulfonic acid. Hydrogen sulfide was slowly bubbled in through a gas dispersion tube with vigorous stirring. The reaction was monitored by TLC, which showed complete consumption of the starting material after 18 hours. The solvent was removed under reduced pressure to yield a residue which was triturated with hexanes and dried in vacuo. The product was chromatographed on silica gel using ethylacetate-dichloromethane to provide the heterocyclic product, 7-methoxy-2H-benzopyranspiro-2'-(1',3',4'-thiadiazolidine)-5'-spiroadamantane, in good yield.

Next, sieve dried benzene (50 mL) was stirred under argon during the addition of $CaCO_3$ (3.5 g., 35 mmol). Lead tetracetate (3.5 g., 7.9 mmol) was added in small portions to the white suspension, which was then allowed to stir for 30 minutes at room temperature. A solution of the aforementioned thiadizolidine (2.1 g, 6 mmol) in 50 mL benzene was added dropwise over a one hour period. The mixture was then allowed to stir overnight. Water (200 mL) was added with vigorous stirring. The aqueous layer was extracted with 3×30 mL benzene and the combined organics were washed with 2×40 mL water, 1×40 mL saturated NaCl, and dried over Na$_2$SO$_4$. The solvent was removed in vacuo to yield 3 g of residue which was chromatographed on silica gel with dichloromethane-hexanes to provide the off-white crystalline thiadiazine, 7-methoxy-2H-benzopyranspiro-2'-(1',3',4'-thiadiazine)-5'-spiroadamantane, in good yield.

A mixture of the above thiadizine (1.77 g, 5 mmole) and triphenyl phosphine (3.1 g., 11.7 mmole) was heated in a sealed tube under argon at 150° C. for 18 hours. The contents were dissolved in a small amount of methylene chloride and applied to a silica gel column for flash chromatography using 5% CH$_2$Cl$_2$ - hexanes to yield 7-methoxy-2-adamantylidene-3-chromene. The product was identical in all respects to the chromene obtained by the first synthetic route. It could also be phosphorylated as described above.

The second step in the synthesis of the dioxetanes involves converting the olefin described above to the dioxetane. Preferably, the conversion is effected photochemically by treating the olefin with singlet oxygen ($^1$O$_2$) in the presence of light. $^1$O$_2$ adds across the double bond to form the dioxetane as follows:

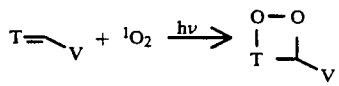

The reaction is preferably carried out at +15° C. in a halogenated solvent, e.g., methylene chloride. $^1$O$_2$ is generated using a photosensitizer. Examples of photosensitizers include polymer-bound Rose Bengal (commercially known as Sensitox II and available from Polysciences) and methylene blue (a well-known dye and pH indicator). The most preferred sensitizer is methylene blue.

The synthesis of the dioxetane having the formula

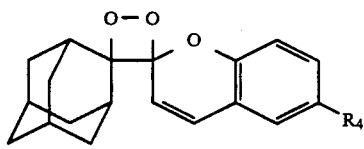

where R$_4$ is a phosphate group follows.

In a large culture tube, 0.075 g (.21 mmole) of the chromene phosphate salt prepared as described above was dissolved in 25 mL CHCl$_3$. A quantity (0.210 g) of methylene blue on silica gel (0.0026 g dye/g SiO$_2$) was added as a sensitizer. The tube was placed in a silvered Dewar flask containing a 250 watt, high-pressure sodium lamp inside a water-cooled immersion well. A piece of 5 mil Kapton (Dupont) placed inside the well served as a U.V. filter. Ice water was pumped through the apparatus to maintain the sample temperature below 15° C. A continuous stream of dry oxygen was passed into the reaction vessel through a capillary tube. The gas flow was adjusted so as to just maintain a uniform suspension of solid-phase sensitizer. After 25 minutes irradiation time, the U.V. absorption of the starting material disappeared. The light yellow-green solution was filtered, evaporated, and reconstituted with 10 mL water. The aqueous sample was then filtered through 0.45 micron nylon filter and chromatographed on a reverse phase, C18 preparative HPLC column using a water/acetonitrile gradient. The appropriate fractions were combined and lyophillized to provide the dioxetane, dispiro(adamantane-2)-3'-(1',2' dioxetane)-4',2''-(7''-phosphoryloxy-3''-chromene) sodium salt, as a white, hygroscopic solid.

Use

A wide variety of assays exist which use visually detectable means to determine the presence or concentration of a particular substance in a sample. The above-described dioxetanes can be used in any of these assays. Examples of such assays include immunoassays to detect antibodies or antigens, e.g., α or β-hCC; enzyme assays; chemical assays to detect, e.g., potassium or sodium ions; and nucleic acid assays to detect, e.g., viruses (e.g., HTLV III or cytomegalovirus, or bacteria (e.g., E. Coli)).

When the detectable substance is an antibody, antigen, or nucleic acid, the enzyme is preferably bonded to a substance having a specific affinity for the detectable substance (i.e. a substance that binds specifically to the detectable substance), e.g., an antigen, antibody, or nucleic acid probe, respectively. Conventional methods, e.g., carbodiimide coupling, are used to bond the enzyme to the specific affinity substance; bonding is preferably through an amide linkage.

In general, assays are performed as follows. A sample suspected of containing a detectable substance is contacted with a buffered solution containing an enzyme bonded to a substance having a specific affinity for the detectable substance. The resulting solution is incubated to allow the detectable substance to bind to the specific affinity portion of the specific affinity-enzyme compound. Excess specific affinity-enzyme compound is then washed away, and a dioxetane is added. In the case of an oxido-reductase enzyme, the O—O peroxy bond of the dioxetane is cleaved, causing the dioxetane to decompose into 2 ketones, one of which contains the chromophore, e.g., coumarin; the chromophore is thus excited and luminesces. Luminescence is detected using, e.g., a photomultiplier tube detector or camera luminometer, as an indication of the presence of the detectable substance in the sample. Luminescence intensity is measured to determine the concentration of the substance.

Where group T or group V contains an enzyme-cleavable group, e.g., phosphate, the enzyme, e.g., phosphatase, cleaves this group to cause luminescence as described above.

When the detectable substance is an enzyme, a specific affinity substance is not necessary. Instead, a dioxetane is used. Therefore, an assay for the enzyme involves adding the dioxetane to the enzyme-containing sample, and detecting the resulting luminescence as an indication of the presence and the concentration of the enzyme.

Examples of specific assays follow.

A. Assay for Human IgG

A 96-well microtiter plate is coated with sheep anti-human IgG (F(ab)$_2$ fragment specific). A serum sample containing human IgG is then added to the wells, and the wells are incubated for 1 hr. at room temperature. Following the incubation period, the serum sample is removed from the wells, and the wells are washed four times with an aqueous buffer solution containing 0.15 M NaCl, 0.01 M phosphate, and 0.1% bovine serum albumin (pH 7.4).

Horseradish peroxidase bonded to anti-human IgG is added to each well, and the wells are incubated for 1 hr. The wells are then washed four times with the above buffer solution, and a buffer solution of a dioxetane is added. The resulting luminescence caused by enzymatic degradation of the dioxetane is detected in a luminometer, or with photographic film in a camera luminometer.

Similar results are obtained using a phosphate-containing dioxetane and alkaline phosphatase in place of horseradish peroxidase.

B. Assay for hCG

Rabbit anti-α hCG is adsorbed onto a nylon-mesh membrane. A sample solution containing hCG, e.g., urine from a pregnant woman, is blotted through the membrane, after which the membrane is washed with 1 ml of a buffer solution containing 0.15 M NaCl, 0.01 M phosphate, and 0.1% bovine serum albumin (pH 7.4).

Microperoxidase-labelled anti-β-hCG is added to the membrane, and the membrane is washed again with 2 ml of the above buffer solution. The membrane is then placed in the cuvette of a luminometer or into a camera luminometer, and contacted with a dioxetane. The luminescence resulting from enzymatic degradation of the dioxetane is then detected.

Similar results are obtained using alkaline phosphatase-labelled anti β-hCG and a phosphate-containing dioxetane.

C. Assay for Serum Microperoxidase 2.7 ml of an aqueous buffer solution containing 0.84 M 2-methyl-2-aminopropanol is placed in a 12×75 mm pyrex test tube, and 0.1 ml of a serum sample containing microperoxidase added. The solution is then equilibrated to 30° C. 0.2 ml of a dioxetane is added, and the test tube immediately placed in a luminometer to record the resulting luminescence. The level of light emission will be proportional to the rate of microperoxidase activity.

The above-described assay can be used to detect serum alkaline phosphatase by using a phosphate-containing dioxetane.

D. Nucleic Acid Hybridization Assay

A sample of cerebrospinal fluid (CSF) suspected of containing cytomegalovirus is collected and placed on a nitrocellulose membrane. The sample is then chemically treated with urea or guanidinium isothiocyanate to break the cell walls and to degrade all cellular components except the viral DNA. The strands of the viral DNA thus produced are separated and attached to the nitrocellulose filter. A DNA probe specific to the viral DNA and labelled with horseradish peroxidase is then applied tot he filter; the probe hybridizes with the complementary viral DNA strands. After hybridization, the filter is washed with an aqueous buffer solution containing 0.2 M NaCl and 0.1 mM Tris-HCl (pH=8.0) to remove excess probe molecules. A dioxetane is added and the resulting luminescence from the enzymatic degradation of the dioxetane is measured in a luminometer or detected with photographic film.

Similar results are obtained using alkaline phosphatase to label the DNA probe, and a phosphate-containing dioxetane.

Other embodiments are within the following claims.

For example, the specific affinity substance can be bonded to the dioxetane through group T or group V, instead of the enzyme. In this case, the group to which the specific affinity substance is bonded is provided with, e.g., a carboxylic acid, amino, or maleimide substituent to facilitate bonding.

Group T or group V of the dioxetane can be bonded to a polymerizable group, e.g., a vinyl group, which can be polymerized to form a homopolymer or copolymer.

Group T or group V of the dioxetane can be bonded to, e.g., membranes, films, beads, or polymers for use in immuno- or nucleic acid assays. The groups are provided with, e.g., carboxylic acid, amino, or maleimide substituents to facilitate bonding.

Group T or group V of the dioxetane can contain substituents which enhance the kinetics of the dioxetane peroxidase-induced degradation, e.g., electron-rich moieties (e.g., methoxy).

Another example of a chemical synthesis involves converting the olefin precursor to a 1,2 bromohydroperoxide by reacting the olefin with $H_2O_2$ and dibromantin (1,3-dibromo-5,5-dimethyl hydantoin). Treatment of the 1,2-bromohydroperoxide with base, e.g., OH or silver salts, e.g., silver bromide, forms the dioxetane.

Rather than treating the olefin with photochemically generated singlet oxygen, the dioxetane can be prepared by treating the olefin with triphenyl phosphite ozonide or triethylsilyl hydrotrioxide, as described in Posner et al., J. Am. Chem. Soc. 109:278–79 (1987).

Another method of synthesizing the olefin precursor involves the McMurray reaction in which the chromophore and carbonyl form of group T olefin are reacted with $TiCL_3/LAH$ to form the olefin. Modified McMurray reactions, e.g., where $TiCl_4/TMEDA/Zn$ is used instead of $TiCl_3LAH$, can also be used.

We claim:

1. A dioxetane compound of the formula:

(a)    (b)

wherein T is a polycycloalkylidene group having 2 or more fused rings, each ring independently having between 5 and 12 carbon atoms, spirally bound to the 3-carbon atom of the dioxetane ring; and V and V', exclusive of the bond(s) joining them to the dioxetane ring, are each a 1,2-chromenyl group of the formula:

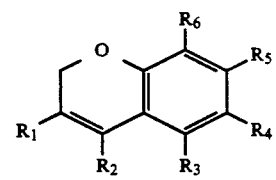

V being non-spirally bound and V' being spirally bound via the 2-carbon atom of the 1,2-chromene ring to the 4-carbon atom of the dioxetane ring, wherein each of $R_1$ to $R_6$, inclusive, is independently hydrogen, an electron-withdrawing group, an electrondonating group, benzoxazole, benzthiazole, benzimidazole, or benztriazole, or two or more of $R_1$ or $R_6$, inclusive, together form a ring.

2. A dioxetane compound of claim 1 wherein the electron-withdrawing group is a perfluoroalkyl group having from 1 to 7 carbon atoms, inclusive, a halogen atom, a carboxyl group, an $SO_3H$, $NO_2$ or $C\equiv N$ group, or a $ZCO_2H$, $ZSO_3H$, $ZNO_2$ or $ZC\equiv N$ group wherein Z is a branched or straight chain alkylene group having from 1 to 7 carbon atoms, inclusive, or an arylene group.

3. A dioxetane compound of claim 1 wherein the electron donating group is branched or straight chain alkoxy group having from 1 to 7 carbon atoms, inclusive, phenoxy, a branched or straight chain hydroxalkyl group having from 1 to 7 carbon atoms, inclusive, hydroxyphenyl, a branched or straight chain alkyl ester group having from 1 to 7 carbon atoms, inclusive, or benzoate, 4. A dioxetane compound of claim 1 wherein at least one of T, or $R_1$–$R_6$, inclusive, independently comprises an enzyme cleavable group having a bond that can be cleaved by an enzyme to yield an electron-rich moiety bonded to the dioxetane ring.

5. A dioxetane compound of claim 4 wherein the enzyme cleavable group is a phosphate ester group.

6. A dioxetane compound of claim 4 wherein the enzyme-cleavable group is an acyl ester group.

7. A dioxetane compound of claim 4 wherein the enzyme-cleavable group is a D-hexopyranoside group.

8. A dioxetane compound of claim 4 wherein $R_1$-$R_3$, inclusive, and $R_6$ are hydrogen, one of $R_4$ and $R_5$ is an enzyme cleavable group, and the other of $R_4$ and $R_5$ is hydrogen.

9. A dioxetane compound of claim 8 wherein the enzyme cleavable group is a phosphate ester group.

10. A dioxetane compound of claim 8 wherein the enzyme cleavable group is an acyl ester group.

11. A dioxetane compound of claim 8 wherein the enzyme cleavable group is a D-hexopyranoside group.

12. A dioxetane compound of the formula:

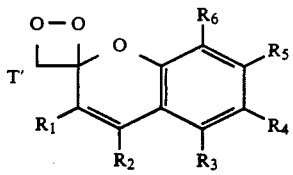

wherein T' is an adamantylidene group; and each of $R_1$ to $R_6$, inclusive, is independently hydrogen, an electron-withdrawing group, an electron-donating group, benzoxazole, benzthiazole, benzimidazole or benztriazole, or two or more of $R_1$ to $R_6$, inclusive, together form a ring.

13. A dioxetane compound of claim 12 wherein one of $R_1$-$R_6$, inclusive, independently comprises an enzyme cleavable group having a bond that can be cleaved by an enzyme to yield an electron-rich moiety bonded to the dioxetane ring.

14. A dioxetane compound of claim 13 wherein the enzyme cleavable group is a phosphate ester group.

15. A dioxetane compound of claim 13 wherein the enzyme cleavable group is an acyl ester group.

16. A dioxetane compound of claim 13 wherein the enzyme cleavable group is a D-hexopyranoside group.

17. A dioxetane compound of claim 12 wherein $R_1$-$R_3$, inclusive, and $R_6$ are hydrogen, one of $R_4$ and $R_5$ is an enzyme cleavable group, and the other of $R_4$ and $R_5$ is hydrogen.

18. A dioxetane compound of claim 17 wherein the enzyme cleavable group is a phosphate ester group.

19. A dioxetane compound of claim 17 wherein the enzyme cleavable group is an acyl ester group.

20. A dioxetane compound of claim 17 wherein the enzyme cleavable group is a D-hexopyranoside group.

21. Dispiro(adamantane-2)-3'-(1',2'-dioxetane)-4',2"-(3"-chromene).

22. A dioxetane compound having the formula:

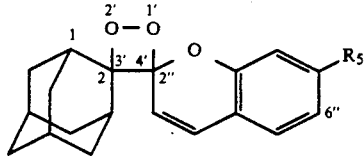

wherein $R_5$ is an enzyme cleavable group having a bond that can be cleaved by an enzyme to yield an electron-rich moiety bonded to the dioxetane ring.

23. A dioxetane compound of claim 22 wherein the enzyme cleavable group is a phosphate ester group.

24. A dioxetane compound of claim 22 wherein the enzyme cleavable group is an acyl ester group.

25. A dioxetane compound of claim 22 wherein the enzyme cleavable group is a D-hexopyranoside group.

26. Dispiro(adamantane-2)-3'-(1',2'-dioxetane)-4',2"-(7"-phosphoryloxy-3"-chromene).

27. A dioxetane compound having the formula:

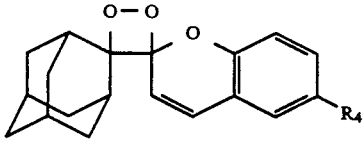

wherein $R_4$ is an enzyme cleavable group having a bond that can be cleaved by an enzyme to yield an electron-rich moiety bonded to the dioxetane ring.

28. a dioxetane compound of claim 27 wherein the enzyme cleavable group is a phosphate ester group.

29. A dioxetane compound o claim 27 wherein the enzyme cleavable group is an acyl ester group.

30. A dioxetane compound of claim 27 wherein the enzyme cleavable group is a D-hexopyranoside group.

31. Dispiro(adamantane-2)-3'-(1',2'-dioxetane)-4',2"-(6"-phosphoryloxy-3"-chromene).

* * * * *